(12) United States Patent
White et al.

(10) Patent No.: US 8,512,385 B2
(45) Date of Patent: Aug. 20, 2013

(54) BONE PLATE WITH COMPLEX, ADJACENT HOLES JOINED BY A BEND RELIEF ZONE

(75) Inventors: Patrick White, West Chester, PA (US); Patrick Berdoz, Chester Springs, PA (US); Steve Forbes, Exton, PA (US)

(73) Assignee: Swiss Pro Orthopedic SA, Bienne (CH)

( * ) Notice: Subject to any disclaimer, the term of this patent is extended or adjusted under 35 U.S.C. 154(b) by 1084 days.

(21) Appl. No.: 12/307,128

(22) PCT Filed: Jul. 6, 2007

(86) PCT No.: PCT/IB2007/001883
§ 371 (c)(1),
(2), (4) Date: Dec. 31, 2008

(87) PCT Pub. No.: WO2008/007194
PCT Pub. Date: Jan. 17, 2008

(65) Prior Publication Data
US 2009/0318921 A1   Dec. 24, 2009

Related U.S. Application Data

(60) Provisional application No. 60/806,731, filed on Jul. 7, 2006, provisional application No. 60/806,733, filed on Jul. 7, 2006.

(51) Int. Cl.
*A61B 17/80* (2006.01)
(52) U.S. Cl.
USPC ............. 606/280; 606/70; 606/283; 606/284
(58) Field of Classification Search
USPC .............................. 606/280–282, 286, 70, 71
See application file for complete search history.

(56) References Cited

U.S. PATENT DOCUMENTS

| | | | |
|---|---|---|---|
| 3,659,959 A | 5/1972 | Haboush |
| 3,716,050 A | 2/1973 | Johnston |
| 4,696,290 A | 9/1987 | Steffee |
| 5,002,544 A | 3/1991 | Klaue et al. |
| 5,261,910 A | 11/1993 | Warden et al. |
| 5,324,290 A | 6/1994 | Zdeblick et al. |

(Continued)

FOREIGN PATENT DOCUMENTS

| | | |
|---|---|---|
| DE | 4341980 A1 | 6/1995 |
| WO | WO0154601 | 8/2001 |
| WO | WO 2006089695 A1 * | 8/2006 |

*Primary Examiner* — Kevin T Truong
*Assistant Examiner* — Christine Nelson
(74) *Attorney, Agent, or Firm* — Michael F. Scalise

(57) ABSTRACT

A bendable bone plate (10) is disclosed which is adapted for use in situ as a conformable bone splint to fix the spatial relationship of at least two bone parts (80). The bone plate (10) has an elongated plate (11) made of a bendable material. A plurality of screw apertures (24) extending through the top (14) and bottom (16) surfaces are disposed along the length (L) of the plate. Bone screws (28) are inserted through the apertures into the underlying bone parts (80) to anchor the elongated plate (11) to the bone parts (80). At least two of the screw apertures (24) are disposed as a closely spaced pair (40) of screw apertures (24) with a "bend relief zone" (60) disposed between the closely spaced apart screw apertures (24). The bend relief zone (60) is disposed to allow the elongated plate (11) to be bent across the bend relief zone (60) up to a certain angle (A) without deforming the screw apertures (24) adjacent the bend relief zone (60).

16 Claims, 7 Drawing Sheets

(56) References Cited

U.S. PATENT DOCUMENTS

| | | |
|---|---|---|
| 5,364,399 A | 11/1994 | Lowery et al. |
| 5,681,311 A | 10/1997 | Foley et al. |
| 5,709,686 A | 1/1998 | Talos et al. |
| 5,733,287 A | 3/1998 | Tepic et al. |
| 2003/0040748 A1* | 2/2003 | Aikins et al. .................... 606/70 |
| 2005/0015089 A1* | 1/2005 | Young et al. .................... 606/69 |
| 2005/0216008 A1* | 9/2005 | Zwirnmann et al. ............ 606/69 |

* cited by examiner

BONE PLATE WITH COMPLEX, ADJACENT HOLES JOINED BY A BEND RELIEF ZONE

CROSS-REFERENCE TO RELATED APPLICATIONS

The present application claims the benefit of prior filed U.S. Provisional Patent Application, Ser. Nos. 60/806,731 filed 7 Jul. 2006, and 60/806,733 also filed 7 Jul. 2006, which applications are incorporated herein by reference.

FIELD OF THE INVENTION

The present invention is in the field of surgically implanted orthopedic devices, implants and prostheses used in orthopedic surgery. More specifically, the present invention relates to bone plates used to reinforce fractured bones and thus to promote healing.

BACKGROUND OF THE INVENTION

A compressive screw system, also known as the DCS system, is a bone plate system that has been used in trauma surgery for many years. The procedures for use of this system are well documented by the AO Institute (Davos, Switzerland), an institute having as one of its goals, the promotion of new orthopedic surgical procedures. This system included a bone plate having slots communicating therethrough. A land in which the slot is wider at one end defines a stepped surface adjacent the portion of the slot that extends through the bone plate. The stepped surface is generally cut with a spherical endmill, thus creating a spherical stepped surface.

In a still further development, bone plates exist which have individual threaded apertures and non-threaded apertures interspersed along the length of the plate. In this and other designs, the distance between holes has become a standard. Although an improvement over the inserts noted above, the locking positions are pre-defined and only available in limited locations, which also reduce surgical flexibility. In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert designs rely on a friction lock via contact between two simple surfaces. Simple surface friction locks are not reliable and come loose more easily than threaded locked holes. The result of such a design is inferior to that of the threaded plate and screw designs discussed below.

In U.S. Pat. No. 5,002,544, there is shown an osteosynthetic pressure plate having a cross-section transverse to the longitudinal axis of the plate at least at one point being wider toward the upper surface than toward the lower surface and the plate having recesses in the lower surface so that upon application to a bone there is space between the bone and the plate. The cross-section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

Further, U.S. Pat. No. 5,709,686 describes a bone plate that has recesses or reduced thickness portions on its sides, between threaded apertures. Although the purpose is not specifically described, these recesses appear to function to avoid warping of the threaded portions when the bone plate is bent. However, when such a bone plate is fixed to a bone, these discontinuous recesses are exposed and may potentially come into contact with and potentially aggravate muscle tissue.

Still further, U.S. Pat. No. 5,733,287 shows, in FIG. 4, a plate that has transverse cuts 13 and a longitudinal cut 14 on the lower surface 7 to reduce contact between the plate and bone. Due to the transverse undercuts 13, the cross-section between the holes is already significantly reduced and therefore is not further decreased by an additional groove 10 on the upper surface 6 as in the embodiment according to FIG. 3. To avoid a cross-section that is too thin, the groove 10 on the upper surface 6 is made discontinuous in short segmental grooves 16 providing a smooth transition into and out of the holes 8.

In yet another solution, PCT application no. WO 01/54601 combines the features of the DCS system discussed above with a locking screw. Such a system is known as the combi-slot. In this design, the stepped surface of the slot is generally ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

Further, this combi-hole includes two distinct overlapping portions in a single slot. One portion of the slot is suited to receive a standard bone screw, while the other portion of the slot is suited to receive a threaded peg oriented perpendicular to the top surface of the bone plate. Also, the combi-holes are generally oriented with the threaded portions being on the innermost end of the combination and the unthreaded portions oriented toward the ends of the bone plate. This improvement increased the flexibility of choice available to orthopedic surgeons using the device in that it was more likely that a hole would be present at a suitable anchoring point in the bone plate. Nevertheless, there are often trauma situations that are best served by the threaded portion being at the extreme ends of the bone plate and/or at various positions throughout the plate. In addition, sometimes there is no specific center of the facture-in such a situation; use of the combi-hole design is limited. The combi-hole if further limited in that it allows the fixing of a screw in either the slotted portion or the threaded portion, but not both.

While patent application no. WO 01/54601 has proven advantageous because screws can be locked to the plate; the presence of an unthreaded slot limits the user's ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

U.S. Pat. No. 5,324,290 shows a complex bone plate having slots with countersunk circular recessed cuts at intervals along the slot (a similar arrangement is shown in U.S. Pat. No. 4,696,290). It further shows the bone plate torqued against the bone so as to at least marginally, conform to the shape of the bone (see FIG. 2). Other patents of interest include U.S. Pat. Nos. 3,716,050; 3,659,595; 5,681,311; 5,261,910, and 5,364, 399, as well as German Patent application DE4341980A1, all showing combinations of conventional slots and recesses which do not fully accommodate a bone screw having a threaded head. In comparison with the combi-hole design and the friction locking design described above, what is needed is a bone plate that provides greater flexibility of choice to the surgeon. More specifically, what is needed is a bone plate that provides this choice of plate placement while reliably and permanently fixing the bone plate to the bone fragments, in any hole position.

What is needed is a bone plate that provides greater flexibility of choice to the surgeon, in a bone plate that has multiple orientations for the locking screw and thus, plate placement, while reliably and permanently fixing the bone plate to the bone fragments, in any hole position.

In addition, what is needed is a versatile bone plate having recesses which determine where the bone plate will bend, in order to avoid the threads in any holes to be bent or warped, while maintaining a smooth external surface.

Finally, what is needed is a bone plate with holes that create bi-directional compression.

SUMMARY OF THE INVENTION

The present invention is bone plates of complex form, for use with a bone plate having a main longitudinal axis, a bone-contacting bottom side and a top side with a plurality of bone screw apertures. At least one pair of the bone screw apertures are closely spaced apart and have a center-to-center distance d which corresponds substantially to the sum of the largest radii (r1+r2) of the two screw apertures, and further defining an unthreaded circular relief joining the holes, or a transverse slot joining the holes. When applied to a bone, two pairs of adjacent adjoining holes are located so as to lie on opposite sides of an osteotomy site. The configuration of this complex bone plate varies, depending on the physiology of the patient.

An object of the invention is to provide a surgeon with the option of placing two bone screws in abutting adjacent positions. Another object of the invention is to provide an orthopaedic surgeon greater flexibility of choice in that a threaded peg or screw providing secure fixing can be positioned at any interval along the bone plate, including at its extreme ends or on its elbow. Another object is to ensure bending along the slot instead of at the threads.

DETAILED DESCRIPTION OF THE INVENTION

Figure 1A:
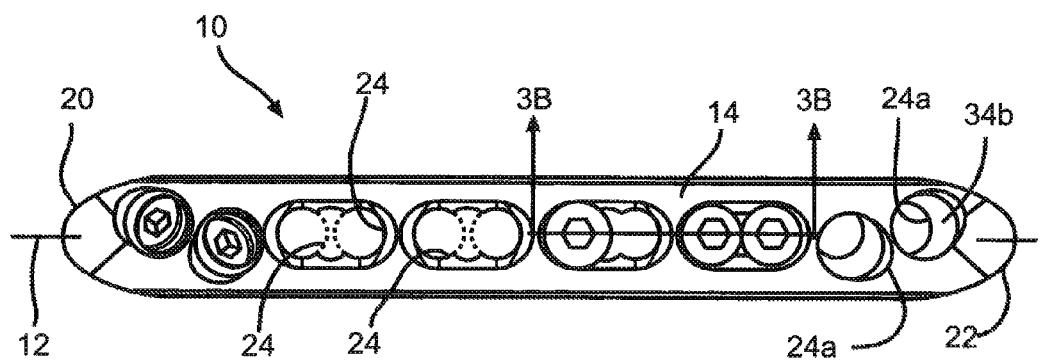
FIGS. 1A and 1B respectively are top views of a bone plate of the invention incorporating one type of bend relief space, and a close-up view of the first end of the bone plate.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1B:
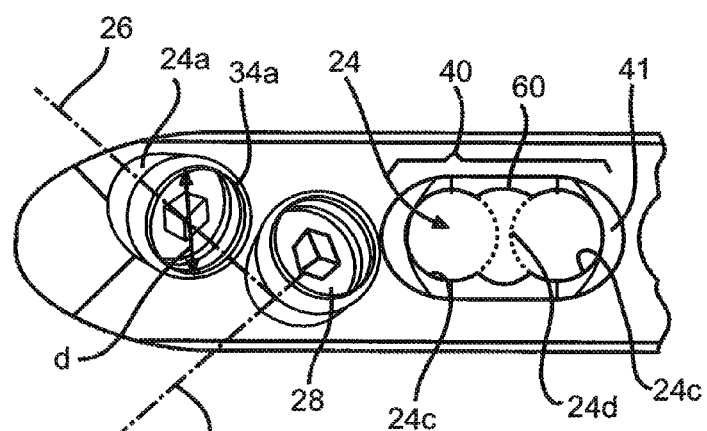
Figure 2A:
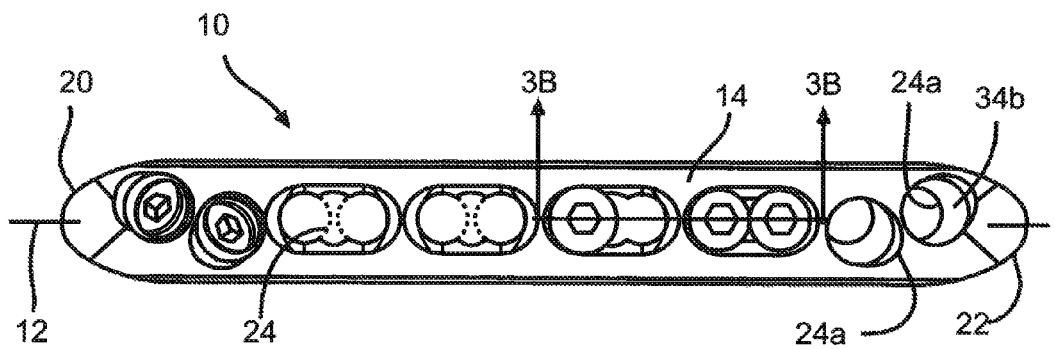
FIGS. 2A and 2B respectively are top views of a bone plate of the invention incorporating an alternative type of bend relief space, and a close-up view of the first end of the bone plate.

As exemplified in FIGS. 1A and 2A, the present bone plate 10 has a main longitudinal axis 12, a bone-contacting bottom side 16 (see FIG. 4), a top side 14 and opposite first 20 and second 22 plate ends. A series of screw apertures 24 extending from the top side 14 of the plate 10 through to its bottom side 16 are formed along the plate axis 12. The screw apertures 24 serve as bone screw guides through which points bone screws 28 are inserted into underlying bone to anchor the bone plate 10 to different parts or fragments of a bone 80 to be reinforced by the bone plate 10 (see FIG. 5). The screw apertures 24 have a screw axis 26 (the general path that a screw takes when inserted through the aperture) which is either perpendicular or angled (see FIGS. 1B and 2B) relative to the plane of the bone plate 10 in the vicinity of the screw aperture 24 depending on the need of a particular application or surgical protocol. Additionally, the bone plate 10 of the present invention has one or more bend relief zones 60 separating certain closely spaced apart screw apertures 24.

Figure 2B:
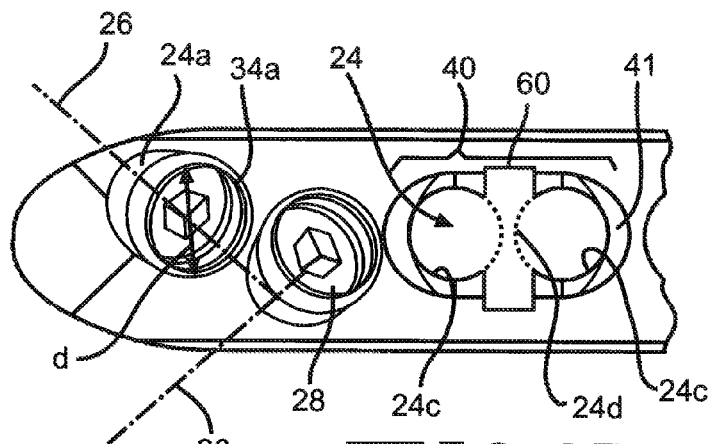

Additionally, the present bone plate 10 includes angled screw apertures 24a. Referring now to FIGS. 1B and 2B, two angled apertures 24a, preferably positioned proximate the plate ends 20, 22 of the bone plate 10, have screw axes 26 that are angled from perpendicular of the plane of the bone plate 10 in opposing orientations. The orientation is selectable by one of skill in the field to provide an optimal utility for a variety of operative procedures. In this particular embodiment, the angled holes 24a in the plate ends 20, 22 are inclined at an angle of approximately forty-five degrees relative to the plane of the topside 14 of the bone plate 10, which passes through the longitudinal axis 12. The angled apertures 24a are disposed relative to each other to accept and to guide a bone screw 28 at opposing angles in order to securely anchor the bone plate 10 to the bone fragment 80 (see FIG. 5).

Figure 3A:
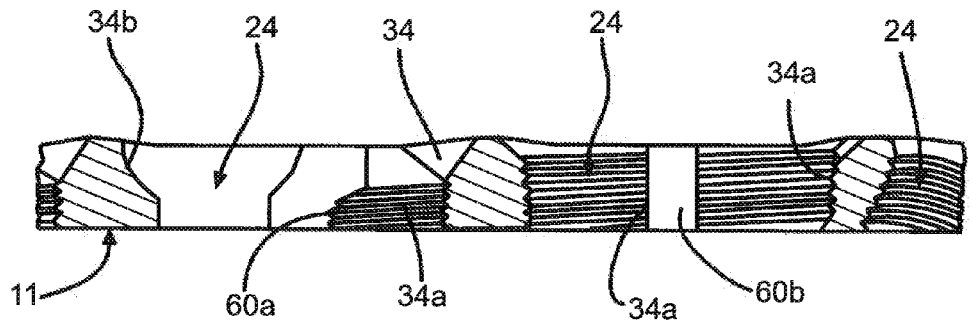
FIGS. 3A and 3B are cross-sectional side views of a section of the bone plate of FIGS. 1A and 2A taken along line 3B and illustrating a location for the bend relief space.
Figure 3B:
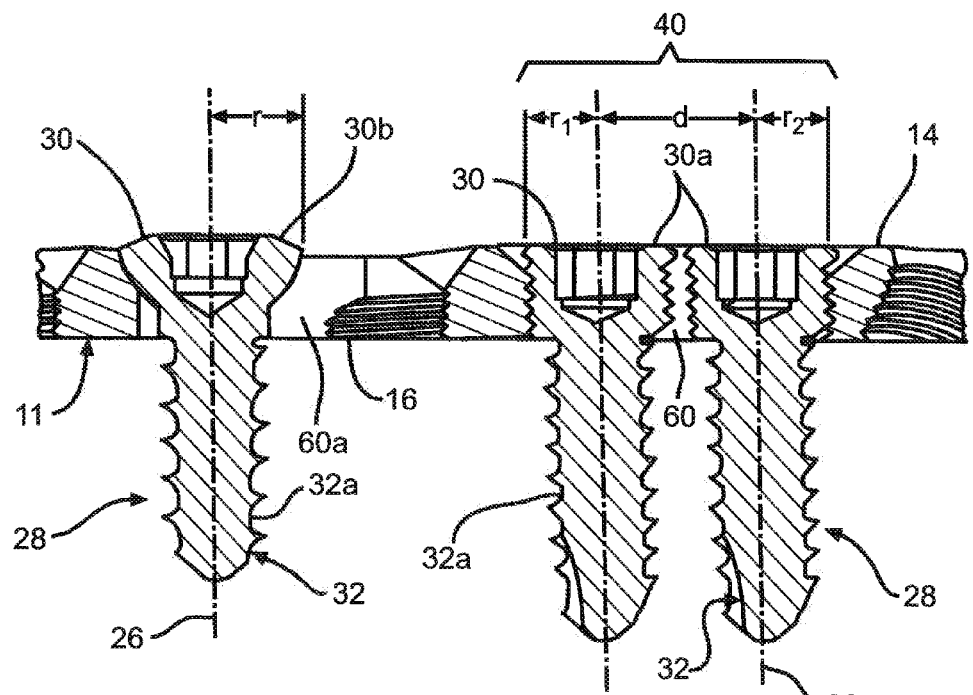
Figure 6A:
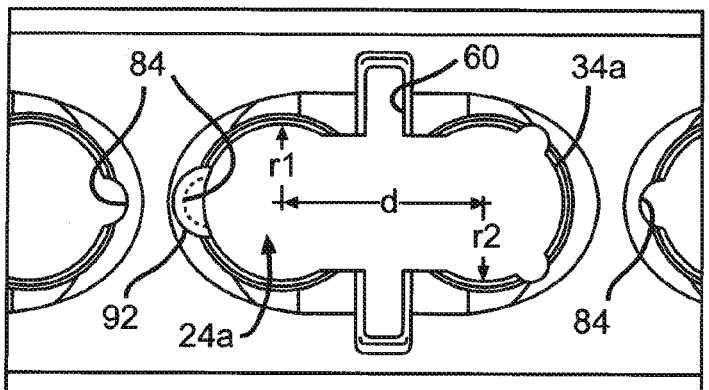
FIGS. 6A and 6B are top-side and bottom-side plan views detailing respective portions of the present bone plate.

Referring now to FIG. 3B and to FIG. 6A, the center-to-center distance d of the two screw apertures 24b of the duplex-aperture 40 corresponds substantially to the diameter d of one of the screws 28 in the complex aperture 40. Alternatively, the center-to-center distance d of the two screw apertures 24b of the duplex-aperture 40 corresponds substantially at least to the sum of the radii of the of the two screw apertures 24b, i.e., r1+r2<=d. This configuration (when advantageous to a particular operation) enables the heads of the bone screws 28 to be positioned as close together as possible, and even to be touching.

It should be noted that screw apertures 24 can be configured to be complementary to bone screws 28 having a number of configurations of screw heads 30 and shanks 32. For example, as exemplified in FIGS. 3A and 3B, a bone screw 28 can have a threaded-head 30a or an unthreaded-head 30b. Additionally, a bone screw 28 with a threaded-head 30a can have a threaded-shank 32a or an unthreaded-shank 32b (see FIG. 7). Correspondingly, the screw apertures 24 can have head-seat 34 for receiving a bone screw 28 that is a threaded-seat 34a or an unthreaded-seat 34b to respectively receive a bone screw 28 having a threaded-head 30a or an unthreaded-head 30b. The bone plate 10 may optionally use a locking bone peg 50, i.e., a bone screw 28 with a threaded-head 30a and unthreaded-shank 32b (see FIG. 7). Preferably, the threads cut in the head of the bone pegs 50 are designed so as to lock, with the threaded apertures 34a in order to better ensure rigid fixing of a fracture. The locking feature used can be any of the known methods of locking threads by mechanical means.

Figure 3C:
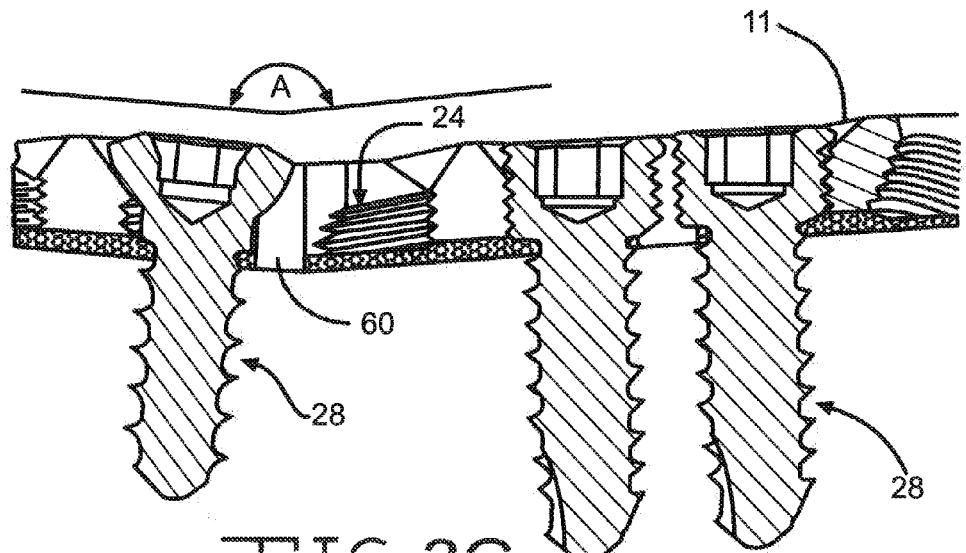
FIGS. 3C and 3D are cross-sectional side views of a section of the bone plate of FIGS. 3B, and illustrate that the bone plate may be bent by an angle A across a bend relief zone and the bending of the plate does not deform the screw apertures, and in 3D, how it interacts with the surface of a bone fragment.
Figure 3D:
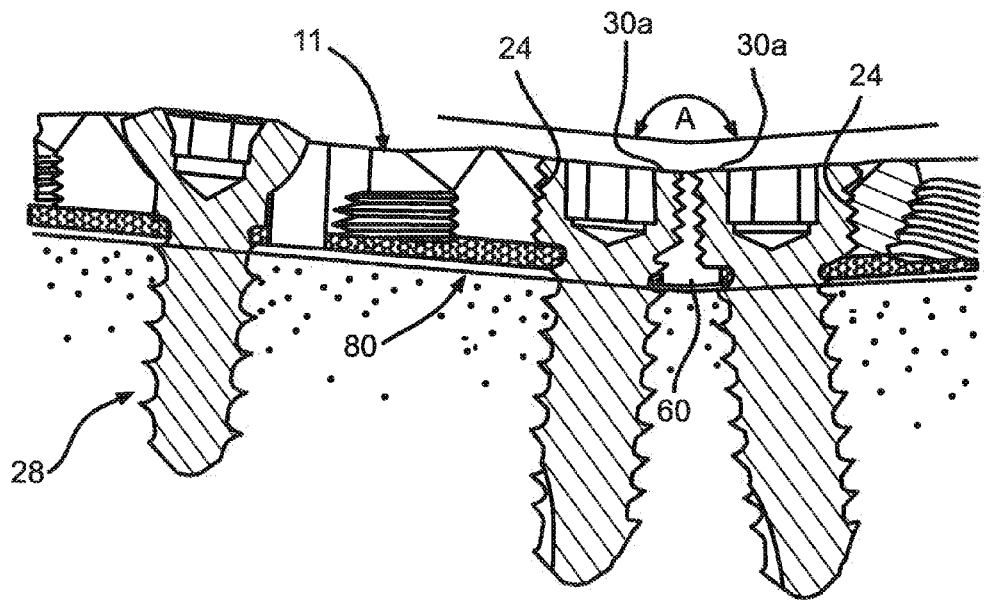

Also, as illustrated in FIGS. 3C and 3D, the elongated plate 11 of the present invention has one or more bend relief zones 60. As exemplified in the figures, particular utility of a bend relief zone 60 as a feature of the present bone plate 10 is that it provides a point on the bone plate that allows the elongated plate 11 to be more easily and controllably bent. More particularly, a bend relief zone 60 is disposed between certain, closely spaced apart screw apertures 24. A bend relief zone 60 so disposed enables the bone plate 10 to be bent by an angle A across the bend relief zone 60 without deforming the screw apertures 24 adjacent the bend relief zone 60. As shown in the figures, bend relief zones 60 can be provided at different locations on the elongated plate 11. In the embodiments illustrated, the bend relief zones 60 are arranged perpendicular to the axis 12 of the bone plate, but could also be at an angle across the axis 12. The present bend relief zone 60 is a part of the bone plate 10 that has sufficient material removed from around the axis 12 of the bone plate 10 to create a relief zone in the material of the bone plate 10 that is more readily bent than the material defining an adjacent screw aperture 24. The bend relief zones 60 of the present invention allow the precise bending of a bone plate 10 to less than an angle A without distortion of the threaded portion of the head-seat 34 of adjacent screw apertures 24. It should be noted that because bone plate 10 is intended to be distortable at the bend relief zone 60, the bend relief zone 60 is never threaded. An advantage of this feature is that a surgeon is able to install two bone screws 28 with threaded-heads 30a substantially side by side, substantially abutting one another. This would be difficult to accomplish in a plate having threaded-seat screw apertures without a bend relief zone, and is impossible to accomplish in a bone plate with overlapping threaded holes (i.e., their center to center distance being less than d).

Figure 4:
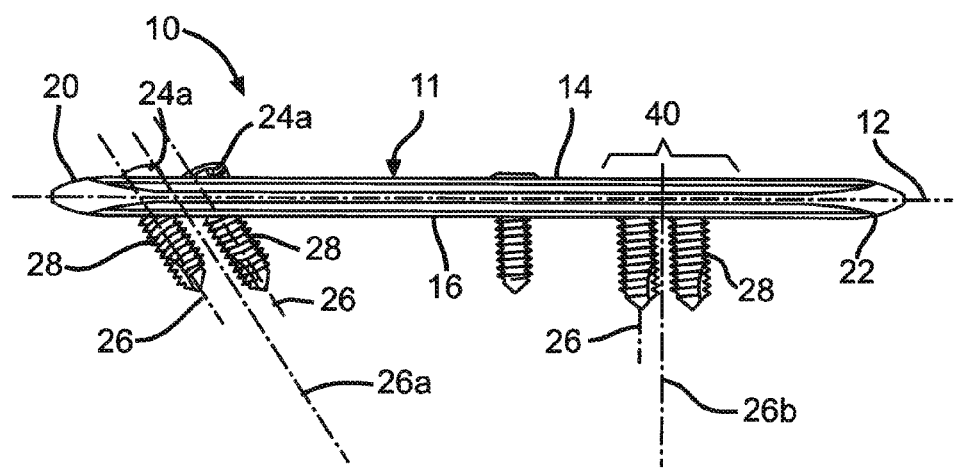
FIG. 4 is a side view of an exemplary assembly of the screws and bone plate of the present invention.

In the embodiment illustrated in FIG. 4, a pair of angled screw apertures 24a is shown at the first plate end 20 of a bone plate 10 with bone screws 28 installed through them. In another preferred embodiment, a pair of angled screw apertures 24a can be disposed at both first and second plate ends 20, 22 of a bone plate 10. In this embodiment, the screw axes 26 of the angled screw apertures 24a at the first plate end 20 slant toward the second plate end 22. This general configuration of the bone screw axes 26a, 26b forms a triangular truss-like structure with the axis 12 of the elongated plate 11 that is able to resist a wide range of forces which could otherwise tend to loosen an installed bone plate 10. Consequently, this configuration resists pull-out forces coming from a wider range of directions. Although FIG. 4 shows the screw axes 26 of the angled screw apertures 24a at the first plate end 20 slanted toward the second plate end 22, they can slant in the opposite direction as shown in FIGS. 1B and 2B.

Additionally, screw apertures 24 proximate the plate ends 20, 22 are independent of screw apertures 24 located in the mid-section of the bone plate 10.

The bone plate 10 has at least one duplex screw aperture 40 made up of two apertures 24 adjoined by a relief zone 60. Multiplex screw apertures (not shown) made up of more than two screw apertures 24 are anticipated, but at least one pair of the of the screw apertures 24 is separated by a bend relief zone. The bend relief zone in the preferred embodiment of FIGS. 1A and 1B is an oblong relief 60a. In the alternative preferred embodiment of FIGS. 2A and 2B, the bend relief zone 60 is a slot 60b transverse to the axis 12 of the bone plate 10.

Figure 5:
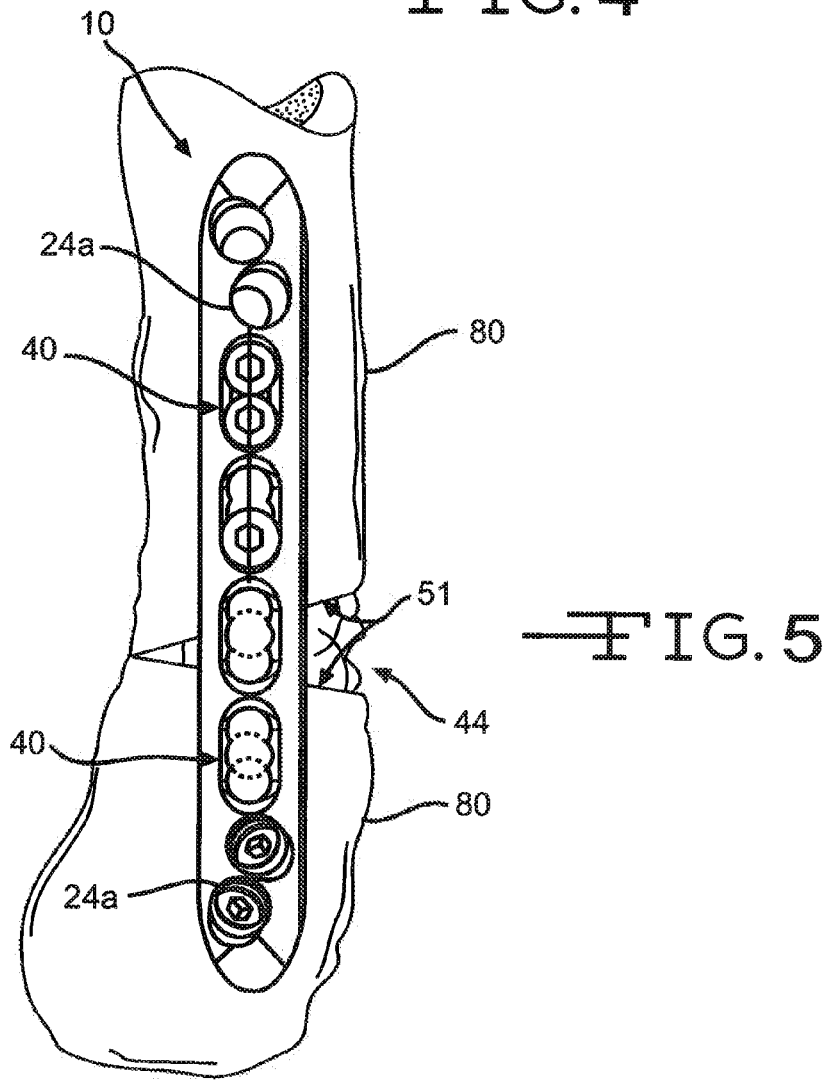
FIG. 5 is a schematic illustration of the present bone plate fixed to a bone.

Referring now to FIG. 5, in another embodiment, the bone plate 10 is particularly suited for femoral osteotomies and/or other corrective osteotomies of the femur. The bone plate 10 has a main longitudinal axis 12, a bone contacting bottom side 16 and a top side 14 with at least two pairs of screw apertures 24. The embodiment shown has multiple pairs of duplex apertures 40 and two pairs of angled apertures 24a. The closely spaced apart pairs of screw apertures 24 of a complex aperture 40 can act as a compression fitting. When applied to a bone part 80, each pair of screw apertures 24 of a complex aperture 40 can be disposed to lie on opposite sides 51 of an osteotomy site 44.

A duplex-aperture 40 preferably has wide bevels 41 on a far and near end with respect to the plate axis 12, and have defined threaded or multifaceted head-seats 34. The bone plate 10 may optionally use a locking bone peg 50, i.e., a bone screw 28 with a threaded-head 30a and unthreaded-shank 32b (see FIG. 7). The threads cut in the head of these pegs 50 are designed so as to lock with the threaded apertures 34a in order to better ensure rigid fixing of a fracture. The locking feature used can be any of the known methods of locking threads by mechanical means.

Figure 1C:
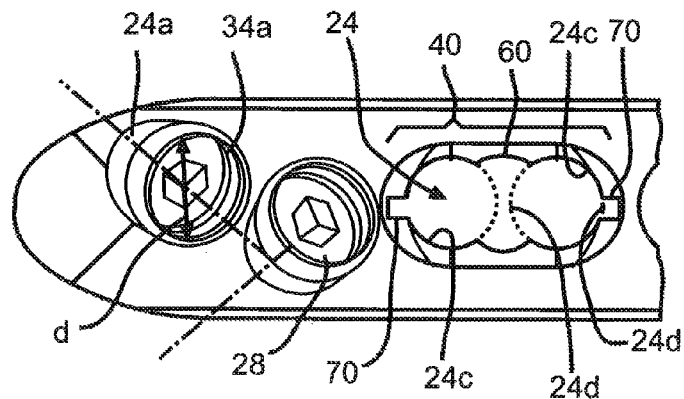
FIG. 1C is a top plan view similar to that of FIG. 1B, but showing an alternative embodiment incorporating the relief-notch feature of the present invention.
Figure 2C:
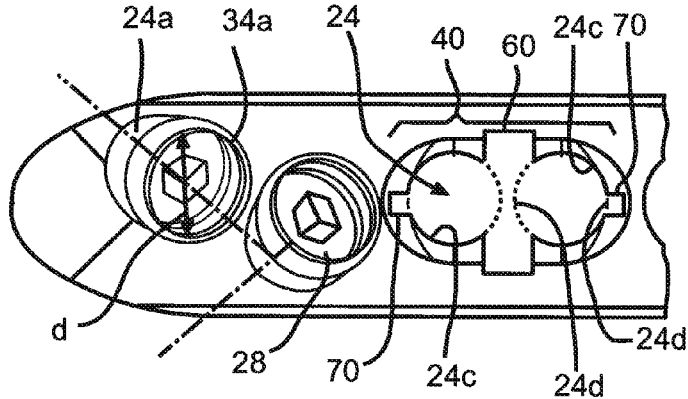
FIG. 2C is a top plan view similar to that of FIG. 2B, but showing an alternative embodiment incorporating the relief-notch feature of the present invention.
Figure 6B:
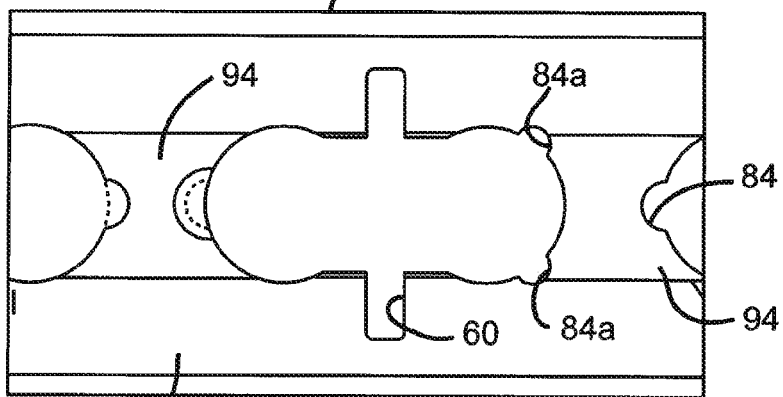
Figure 6C:
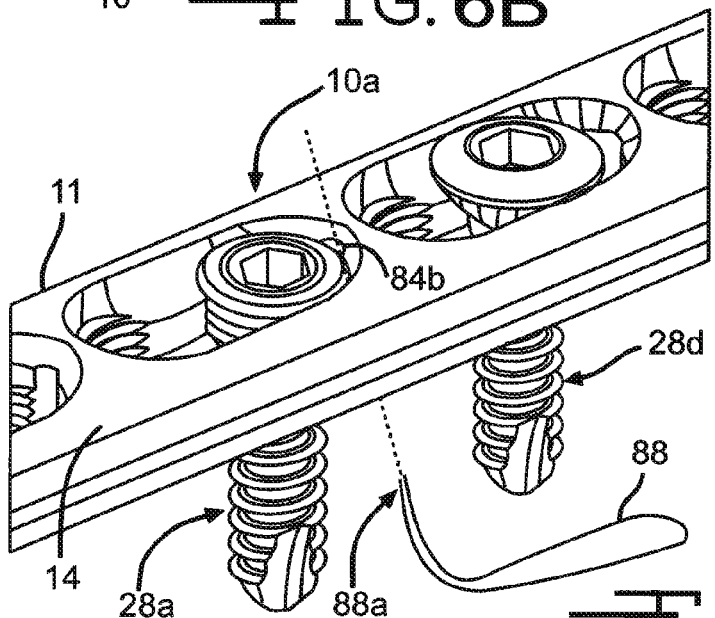
FIG. 6C is a top-side perspective view of a portion of the present bone plate with bone screws inserted into two of the complex apertures.

A preferred embodiment of the present bone plate 10a is illustrated in FIGS. 1C and 2C and in FIGS. 6A to 6C. In this embodiment, the complex apertures 40a are similar to the complex apertures described above, but differ in that they have a relief notch 84 disposed in the screw head seat 34 portion of one or both screw apertures 24. The relief notch 84 provides desirable advantages that are not similarly accomplished in their absence. For example, as shown in FIG. 6A, a self-locking insert 92 can be disposed in the notch 84 to provide increased friction for setting a threaded head bone screw 30a set in a threaded aperture 24a. As also illustrated in FIGS. 6A and 6B, it is intended that a screw aperture 24 may have more than one relief notch 84a. A further example of an advantage of the present notch feature is illustrated in FIG. 6C, which illustrates that a tensioning wire 88 may be looped around a first bone screw 28d, passed along the bottom side 16 of the elongated plate 11 and the ends of the wire 88a drawn up to the top side 14 of the elongated plate 11 through the recess notch 84b in an adjacent second bone screw 28e. In the embodiment illustrated in FIG. 6B, the bottom-side 16 of the elongated plate 11 is provided with a clearance channel 94 recessed into the surface of the bottom-side 16 of the plate 11. The clearance channel 94 communicates with the relief notches 84 to provide a path for the tensioning wire 88 to be easily removed through the relief notch 84a after the bone screws 28d, 28e have been set against the bone plate 10a.

Preferably, the notch feature 84 defines a screw aperture 24 having a threaded screw head seat 34a with at least one threaded surface portion 35 and one unthreaded surface portion 36. In a complex aperture 40a, the notch feature 84 defines a screw aperture 24 in which the threaded screw head seat 34a has at least two threaded surface portions 35 and two unthreaded surface portions 36, with one of the at least two unthreaded surface portions being the relief zone 60.

Figure 7:
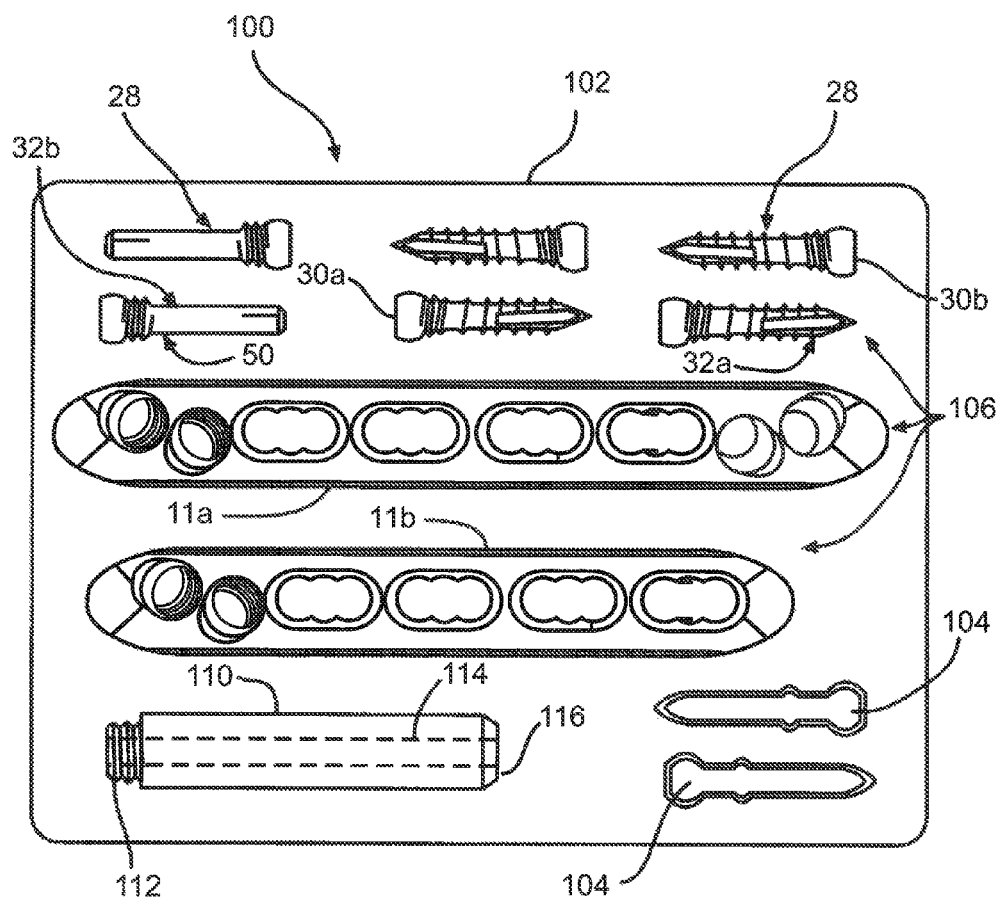
FIG. 7 is a top view of a kit of the present invention.

Referring now to FIG. 7, in another embodiment, an orthopedic bone plate kit 100 includes a compartmented container 102, preferably having shaped compartment spaces 104 corresponding to the shape of the kit item 106 to be received in the shaped compartment space 104. Kit items 106 contained in the kit 100 include one or more bone plates 10 having the same or similar elongated plate features 11a and 11b, and a plurality of bone screws 28. Note that the bone screws 28 may be of a variety of somewhat different configurations practicable with the screw apertures 24 of the present invention. As examples, included in the kit 100 shown are: threaded-head bone screws 30a, unthreaded-head bone screws 30a (both with threaded shanks) and threaded-head pegs 32b (i.e., an unthreaded shank), all can be of various lengths. Additionally shown in the kit 100 is a drill guide 110. The drill guide 110 has a threaded end 112 that can screw into the threaded-seat 34a on a screw aperture 24. The drill guide has a hollow bore 114 that serves as a guide for a drill bit (not shown) for use in drilling a pilot hole in the bone for the bone screw 28 that is to be inserted into the bone through the screw aperture 24.

In another advantage, the invention enables spacing between bone screws 28 that is so close that the surgeon is able to maintain a standard spacing such as that purveyed by the AO Institute (Davos, Switzerland).

In another advantage, where a fracture line runs between adjacent screw apertures 24 of a duplex-aperture 40, a surgeon is able to place a bone screw 28 on opposite sides of the fracture line, thereby better fixing the broken bone together for optimal healing.

In another advantage, the bone plate 10 provides greater flexibility of choice by providing multiple complex screw apertures 24 oriented along the longitudinal axis 12 of the bone plate and/or staggered along the axis 12.

In still another advantage, the threaded apertures 34a of the elongated plate 11 can be provided with a bone screw axis 26 that is perpendicular or angled relative to the top side 14 of the bone plate 10.

In another advantage, the bone plate 10 includes features that further increase the adaptability of the invention to the particular needs of surgery. The configuration of this complex bone plate 10 may vary, depending on the physiology of the patient. An illustration of the flexibility of application of the plate 80 is its flexible use in osteotomy.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A bone plate, comprising:
   a) an elongated plate having a bone contacting bottom surface, a top surface, and a plate thickness between the bottom and top surfaces;
   b) a plurality of screw apertures extending through the plate thickness and into which bone screws are insertable;
   c) at least two of the screw apertures being aligned adjacent to each other along a main axis to thereby provide a complex aperture,
      i) wherein each of the at least two adjacent screw apertures of the complex aperture has a threaded head seat that provides at least a partially threaded portion, and
      ii) wherein a center-to-center distance between the at least two adjacent screw apertures of the complex aperture is greater than a sum of the largest radii of each of them; and
   d) a bend relief zone provided as an open area extending to and meeting the upper plate surface and the lower plate surface to thereby provide open communication between the two adjacent screw apertures,
      i) wherein opposed imaginary secondary axes aligned parallel to the main axis extend through points where the at least two screw apertures meet the open area of the bend relief zone, and
      ii) wherein opposed. portions of a perimeter of the bend relief zone reside on an opposite side of a respective one of the imaginary axes spaced from the main axis.

2. The bone plate of claim 1, wherein the at least two screw apertures of the complex aperture each have a largest aperture radius that extends into the bend relief zone of the complex aperture.

3. The bone plate of claim 1, wherein the bend relief zone permits the bone plate to be controllably bent.

4. The bone plate of claim 1, wherein the bend relief zone permits the bone plate to be bent by an angle (A) across the bend relief zone without deforming the screw apertures comprising the complex aperture adjacent to the bend relief zone.

5. The bone plate of claim 1, wherein the bend relief zone extends at least half way through a width of the elongated plate, the width being measured perpendicular to the main axis of the complex aperture.

6. The bone plate of claim 1, wherein the bend relief zone has a shape selected from the group consisting of: an oblong shaped relief and a slot shaped relief.

7. The bone plate of claim 6, wherein the bend relief zone is a slot transverse to the main axis of the complex aperture.

8. An orthopedic kit comprising:
   a) a compartmented container having compartment spaces for receiving items to be contained in the kit;
   b) a first item of the kit being at least one bone plate of claim 1; and
   c) a second item of the kit being a plurality of bone screws.

9. The bone plate of claim 1 wherein the perimeter of the bend relief zone is a radiused surface on the opposite sides of the respective imaginary axes.

10. The bone plate of claim 1 wherein the perimeter of the bend relief zone is a squared-off slot on the opposite sides of the respective imaginary axes.

11. The bone plate of claim 1 wherein bend relief zone permits the bone plate to be bent to an angle (A) without deforming the threaded head seat of the screw apertures adjacent the bend relief zone.

12. A bone plate, comprising:
   a) an elongated plate having a bone contacting bottom surface, a top surface, and a plate thickness between the bottom and top surfaces, wherein the plate is made of a bendable material and has a longitudinal axis extending along a length and wherein a width is perpendicular to the length and the longitudinal axis;
   b) a plurality of screw apertures extending through the top surface to the bottom surface of the plate, each having a threaded head seat that provides at least a partially threaded portion, wherein at least two of the screw apertures are aligned adjacent to each other along the longitudinal axis to thereby provide a complex aperture;
   c) each screw aperture having a screw axis that is disposed at an acute angle relative to a plane of the bottom surface adjacent to and surrounding the at least two screw apertures comprising the complex aperture; and d) a bend relief zone provided as an open area extending to and meeting with the upper and lower bone plate surfaces to thereby provide open communication between the two adjacent screw apertures,
  i) wherein opposed imaginary secondary axes aligned parallel to the longitudinal axis extend through points where the at least two screw apertures meet the open area of the bend relief zone, and
  ii) wherein opposed portions of a perimeter of the bend relief zone reside on an opposite side of a respective one of the imaginary axes spaced from the main axis.

13. The bone plate of claim 12 wherein the perimeter of the bend relief zone is a radiused surface on the opposite sides of the respective imaginary axes.

14. The bone plate of claim 12 wherein the perimeter of the bend relief zone is a squared-off slot on the opposite sides of the respective imaginary axes.

15. The bone plate of claim 12 wherein bend relief zone permits the bone plate to be bent to an angle (A) without deforming the threaded head seat of the screw apertures adjacent the bend relief zone.

16. A bone plate, comprising:
a) an elongated plate having a bone contacting bottom surface, a top surface, and a plate thickness between the bottom and top surfaces;
b) a plurality of screw apertures extending through the plate thickness and into which bone screws are insertable;
c) at least two of the screw apertures being aligned adjacent to each other along a main axis to thereby provide a complex aperture,
  i) wherein each of the at least two adjacent screw apertures of the complex aperture has a head seat that is a threaded head-seat or an unthreaded head-seat, and
  ii) wherein a center-to-center distance between the at least two adjacent screw apertures of the complex aperture is greater than a sum of the largest radii of each of the respective screw apertures; and
d) a bend relief zone provided as an open area extending to and meeting with the upper and lower bone plate surfaces to thereby provide open communication between the two adjacent screw apertures,
  i) wherein opposed imaginary secondary axes aligned parallel to the main axis extend through points where the at least two screw apertures meet the open area of the bend relief zone, and
  ii) wherein opposed portions of a perimeter of the bend relief zone reside on an opposite side of a respective one of the imaginary axes spaced from the main axis.

* * * * *